(12) United States Patent
Royalty et al.

(10) Patent No.: US 7,851,499 B2
(45) Date of Patent: Dec. 14, 2010

(54) INSECTICIDAL FERTILIZER MIXTURES

(75) Inventors: Reed Nathan Royalty, Cary, NC (US); Britt Baker, Cary, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 11/301,370

(22) Filed: Dec. 13, 2005

(65) Prior Publication Data

US 2007/0135305 A1  Jun. 14, 2007

(51) Int. Cl.
| | |
|---|---|
| A01N 43/56 | (2006.01) |
| A01N 43/58 | (2006.01) |
| A61K 31/415 | (2006.01) |
| C05D 9/00 | (2006.01) |
| C05B 7/00 | (2006.01) |
| C05B 17/00 | (2006.01) |

(52) U.S. Cl. .................. 514/407; 71/31; 71/32; 71/33; 71/34; 71/35; 71/36

(58) Field of Classification Search ............. 504/101, 504/282

See application file for complete search history.

(56) References Cited

U.S. PATENT DOCUMENTS 5,783,203 A * 7/1998 Schutte et al. ............. 424/405
2005/0065034 A1 * 3/2005 Miele et al. ................ 504/367

FOREIGN PATENT DOCUMENTS

JP  2000191407  *  7/2000

OTHER PUBLICATIONS

U.S. Appl. No. 11/041,167, filed Jan. 21, 2005.
Schenck, N.C., et al., "Compatibility of Insecticides, Fungicides, and Foliar Fertilizers on Watermelon", Schenck and Alderez: Watermelon Fertilizers, 1962, 209-212.
Fishel, Frederick M., "Pesticide Interactions", Pesticide Information Office, Florida Cooperative Extension Service, Institute of Food and Agricultural Sciences, University of Florida, PI-145, 2007, 1-3.

* cited by examiner

*Primary Examiner*—Alton N Pryor
(74) *Attorney, Agent, or Firm*—Andrew T. Prokopetz; Richard E. L. Henderson

(57) ABSTRACT

This invention relates to insecticidal fertilizer mixtures containing
(a) an agonist or antagonist of ion channels in the insect nervous system;
(b) a fertilizer;
(c) optionally, an adherent; and
(d) optionally, one or more auxiliaries and/or carrier materials.

4 Claims, No Drawings

INSECTICIDAL FERTILIZER MIXTURES

BACKGROUND OF THE INVENTION

This invention relates to stable and efficacious insecticidal fertilizer mixtures comprising a fertilizing component and an agonist or antagonist of ion channels in the insect nervous system.

Agonists and antagonists of ion channels in the insect nervous system are known. It is also known to use fertilizers in granular form for broadcast application to turfgrass and to use fertilizers for ornamental houseplants in the form of small fertilizer sticks or impregnated cardboard strips that are pressed into the nutrient substrate of the plants. Also known are mixtures of fertilizer granules with insecticides and/or other pesticide products for treatment of turfgrass and tablets containing dimethoate as insecticidal active substance and fertilizer for treatment of ornamental houseplants, but the action of such mixtures is not completely satisfactory. For example, U.S. Pat. No. 5,783,203 describes mixtures containing fertilizers and agonists or antagonists of nicotinergic acetylcholine receptors of insects, but the method described therein, while useful in part because it can provide increased uptake of pesticidally active components into plants, has not been found useful for preparing granular fertilizer mixtures that effectively and rapidly release ion channel agonists or antagonists into the soil. Liquid fertilizer systems, such as those containing agonists or antagonists of nicotinergic acetylcholine receptors described in U.S. patent application Ser. No. 11/041,167, are also known but are not useful for solid fertilizer systems.

SUMMARY OF THE INVENTION

This invention relates to insecticidal fertilizer mixtures comprising
(a) an agonist or antagonist of ion channels in the insect nervous system;
(b) a fertilizer;
(c) optionally, an adherent; and
(d) optionally, one or more auxiliaries and/or carrier materials.

This invention further relates to dimensionally stable mixtures of agonists or antagonists of ion channels in the insect nervous system with fertilizers, optional adherents, and optional auxiliaries and carrier materials in the form of small sticks, plates, tablets or granules, which increase the speed of action of the agonist or antagonist.

DETAILED DESCRIPTION OF THE INVENTION

The action of the mixtures according to the invention begins more rapidly than customary fertilizer-free granules containing the same active ingredient. The mixtures according to the invention can be employed simply and without problems, specifically in non-commercial horticulture.

Active ingredients that are effective according to the invention include agonists or antagonists of ion channels, such as GABA-gated or glutamate-gated chloride (Cl⁻) channels, in the insect nervous system. Examples of suitable ion channel agonists are arylpyrazoles of formula (I)

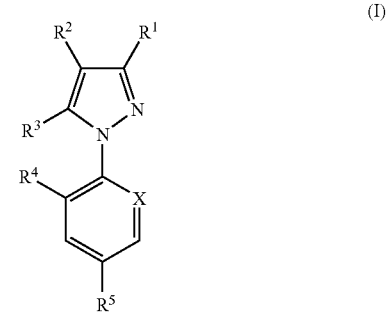

in which
X represents N or C—$R^6$,
$R^1$ is CN, methyl, or halogen,
$R^2$ is $S(O)_n R^7$, 4,5-dicyanoimidazol 2-yl, or haloalkyl,
$R^3$ represents hydrogen, halogen, $NR^8 R^9$, $S(O)_m R^{10}$, $C(O)R^{10}$, $C(O)O$—$R^7$, alkyl, haloalkyl, $OR^{11}$, or —N=$CR^{12}R^{13}$,
$R^4$ and $R^6$, independently of one another, represent hydrogen, halogen, CN, or $NO_2$,
$R^5$ represents halogen, haloalkyl, haloalkoxy, $S(O)_q CF_3$, or $SF_5$,
$R^7$ is alkyl or haloalkyl,
$R^8$ and $R^9$ independently represent hydrogen, alkyl, haloalkyl, C(O)alkyl, alkoxycarbonyl, or $S(O)_r CF_3$; or $R^8$ and $R^9$ together optionally form a divalent alkylene radical that is optionally interrupted by one or two divalent heteroatoms, such as oxygen or sulphur,
$R_{10}$ represents alkyl or haloalkyl,
$R_{11}$ represents hydrogen, alkyl, or haloalkyl,
$R_{12}$ represents hydrogen or alkyl,
$R_{13}$ represents phenyl or heteroaryl that is unsubstituted or optionally substituted by one or more halogen atoms or a member selected from the group consisting of OH, —O-alkyl, —S-alkyl, cyano, and alkyl, and
m, n, q, and r, independently of one another, represent 0, 1, or 2.

Alkyl groups preferably have 1 to 6 carbon atoms and include, for example, methyl, ethyl, i-propyl, and sec.- or t.-butyl. Haloalkyl groups preferably have 1 to 4 (more preferably 1 or 2) carbon atoms and preferably 1 to 5 (more preferably 1 to 3) halogen atoms, where the halogen atoms are identical or different and are preferably fluorine, chlorine, or bromine (more preferably fluorine), and include, for example, trifluoromethyl. Alkoxy groups preferably have 1 to 4 (more preferably 1 or 2) carbon atoms and include, for example, methoxy, ethoxy, n- and i-propyloxy, and n-, i- and t-butyloxy When $R^1$ is methyl, it is generally preferred that either (1) X is N, $R^3$ is $NH_2$, $R^4$ is Cl, $R^5$ is $CF_3$, and $R^7$ is haloalkyl, or (2) X is C—Cl, $R^2$ is 4,5-dicyanoimidazol-2-yl, $R^3$ is Cl, $R^4$ is Cl, $R^5$ is $CF_3$. However, a more preferred group of effective 1-arylpyrazoles of the invention is that wherein X is C—$R^6$; $R^1$ is CN; $R^3$ is $NH_2$; $R^4$ and $R^6$, independently of one another, represent halogen; $R^5$ is haloalkyl; and $R^7$ is haloalkyl. A most preferred 1-arylpyrazole is 5-amino-1-(2,6-dichloro-4-trifluoromethylphenyl)-4-trifluoromethylsulfinyl-3-cyanopyrazole.

The contents of active substance are preferably from about 0.0001% to about 1%, preferably from about 0.001% to about 0.1%, and more preferably from about 0.005% to about 0.015%.

Suitable fertilizer components include organic and inorganic nitrogen-containing compounds such as urea, urea-formaldehyde condensation products, amino acids, ammonium salts and nitrates, as well as potassium salts (preferably chlorides, sulfates, or nitrates) and phosphoric acid and/or salts of phosphoric acids (preferably potassium salts or ammonium salts). The fertilizers may also contain salts of micronutrients (preferably manganese, magnesium, iron, boron, copper, zinc, molybdenum, and/or cobalt) and phytohormones (e.g., vitamin B1 or indole-3-acetic acid). Commercially available complete fertilizers are preferably employed.

The principal fertilizer constituents, nitrogen, potassium, and phosphorus, can be varied within wide limits. It is conventional to use contents of from 1 to 30% of nitrogen (preferably from 5 to 20%), from 1 to 20% of potassium (preferably from 3 to 15%), and from 1 to 20% of phosphorus (preferably from 3 to 10%). The contents of microelements are usually in the ppm range, preferably from 1 to 1000 ppm.

The adherent component serves to establish and/or maintain physical contact between the fertilizer component and the other components of the insecticidal fertilizer mixtures of the invention. When the agonist or antagonist component is soluble in a liquid adherent, the agonist or antagonist component can be initially dissolved or suspended in the adherent and then applied to the fertilizer by any conventional method, such as spraying or simple mixing. When the agonist or antagonist component is not soluble in a liquid adherent, all of the components can first be mixed together until essentially homogenous, after which the adherent is applied in a manner that does not lead to excessive aggregation of solid particles (when the agonist or antagonist component and the fertilizer are solids) or to separation of liquid from solid components (when the agonist or antagonist component is liquid). Suitable adherents are typically retained on the resultant insecticidal fertilizer mixtures, but it is also possible to use adherents that evaporate or are washed away as long as they serve to establish and/or maintain physical contact between components (a) and (b). Suitable adherents include known organic adhesives, including tackifiers, such as celluloses or substituted celluloses, natural and synthetic polymers in the form of powders, granules, or lattices, and inorganic adhesives such as gypsum, silica, or cement. However, it is also possible to use compounds that are not ordinarily considered adhesives as long as they suitably maintain physical contact between the various components. Particularly preferred adherents of this type are citric acid esters, such as Citroflex® esters. It is also possible to use organic or inorganic liquids that dissolve or suspend the agonist or antagonist component but do not persist in substantial quantities, such as water, alcohols, esters, ketones, ethers, aromatics, and other known liquids. When such adherents are used, the insecticidal fertilizer mixtures of the invention retain little if any of the adherent once the mixtures are prepared. Regardless of the type of adherent used, the adherent is generally present in the mixture in concentrations of from 1 to 30% by weight, preferably from 2 to 20% by weight.

Suitable solid carrier materials include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable solid carrier materials for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks. Coated fertilizers can also be used.

Suitable auxiliaries for the preparation of the mixtures according to the invention include disintegrants and surfactants. Disintegrants are used to promote the release of the active substance in the soil. Corn starch, crosslinked polyvinylpyrrolidone, and specific celluloses can be used individually or in combination. Disintegrants are present in concentrations of from 1 to 20% by weight, preferably from 3 to 10% by weight. Surfactants are used to improve the biological activity of the active substance by solubilization. Surfactants are present at a content between 1 to 10% by weight, preferably from 2 to 5% by weight. Nonionic surfactants of the alkyl-aryl-ethoxylate type are appropriate.

Granular fertilizers are particularly preferred. However, the mixtures of active substance, fertilizers, adhesive, auxiliary, and inert substances can, if desired, be mixed intensively and compressed by an extruder into small sticks with a diameter of from 3 to 10 mm, preferably from 6 to 8 mm, and a length of from 1 to 10 cm, preferably from 3 to 6 cm. Alternatively, the mixture can be brought into the desired form of small sticks using a tableting press. It is also possible to produce small sticks or tablets that are free from active substance and then to coat these sticks or tablets with a solution of the active substance. This subsequent coating operation can also be used with advantage to apply active substance to fertilizer granules.

The fertilizer mixtures according to the invention are suitable for the control of insects that are encountered in horticulture, agriculture, and forestry. The fertilizer mixtures are active against normally sensitive and resistant species and against all or individual stages of development. The above-mentioned pests include the following:

From the order of the Siphonaptera, for example, *Ctenocephalides felis, Ctenocephalides canis, Pulex irritans, Spilopsyllus cuniculi, Tunga penetrans,* and *Xenopsylla cheopis.*

From the order of the Acari, for example, *Rhipicephalus sanguineus, Ixodes pacificus, Ixodes scapularis, Amblyomma americanum, Amblyomma maculatum, Dermatocentor andersoni, Dermatocentor variabilis, Haemaphysalis chordeilis,* and *Boophilus annulatus.*

From the order of the Isopoda, for example, *Oniscus asellus, Armadillidium vulgare* and *Porecellio scaber.*

From the order of the Diplopoda, for example, *Blaniulus guttulatus.*

From the order of the Chilopoda, for example, *Geophilus carpophagus* and *Scutigera* spec.

From the order of the Thysanura, for example, *Lepisma saccharina.*

From the order of the Collembola, for example, *Onychiurus armatus.*

From the order of the Orthoptera, for example, *Scapteriscus* spp. such as *Scapteriscus abbreviatus, Scapteriscus acletus, Scapteriscus boreliji, Scapteriscus didactylus,* and *Scapteriscus vicinus, Neocurtilla hexadactyla, Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.*

From the order of the *Dermaptera,* for example, *Forficula auricularia.*

From the order of the *Isoptera*, for example *Reticulitermes* spp.

From the order of the Mallophaga, for example, *Trichodectes* spp. and *Damalinea* spp.

From the order of the Thysanoptera, for example, *Hercinothrips femoralis* and *Thrips tabaci*.

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the *Homoptera*, for example, *Aleurodes brassicae*, *Bemisia tabaci*, *Trialeurodes vaporariorum*, *Aphis gossypii*, *Brevicoryne brassicae*, *Cryptomyzus ribis*, *Aphis fabae*, *Doralis pomi*, *Eriosoma lanigerum*, *Hyalopterus arundinis*, *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella maculipennis*, *malacosoma neustria*, *Euproctis chrysorrhoea*, *Lymantria* spp., *Bucculatrix thurberiella*, *Phyllocnistis citrella*, *Agrotis* spp., *Spodoptera exigua*, *Mamestra brassicae*, *Panolis flammea*, *Prodenia litura*, *Spodoptera* spp., *Trichoplusiani*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*.

From the order of the Coleoptera, for example, *Anobium punctatum*, *Rhizopertha dominica*, *Acanthoscelides obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* pp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon soistitialis* and *Costelytra zealandica*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tanaus* spp., *Tannia* spp., *Bibio hortulanus*, *Oscinella frit*, *Phorbia* spp., *Pegomyia hyoscyami*, *Ceratitis capitata*, *Dacus oleae* and *Tipula paludosa*.

Particularly worthy of mention is the action against ants (particularly fire ants), mole crickets, fleas, ticks, and other yard pests.

The compositions according to the invention are employed in a dose such that from about 0.01 to 100 mg/m$^2$ of active substance, preferably from 0.1 to 10 mg/m$^2$ of active substance and particularly preferably from 0.1 to 5 mg/m$^2$ of active substance, are employed.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all percentages are percentages by weight.

EXAMPLES

Preparation of Test Sample

The following ingredients were used in the following proportions to prepare an insecticidal fertilizer mixture according to the invention:

| Ingredient | Percent by weight (based on total) |
|---|---|
| Fipronil (90%) | 0.008 |
| Citroflex A-4 | 1 |
| Fertilizer | 98.992 |

The fertilizers used in the examples were 15-2-15, 0-0-7, and 24-8-15 fertilizers.

Granular formulations were prepared by dissolving technical grade fipronil in the Citroflex A-4 and then spraying the resultant mixture onto the fertilizer. Mixtures having a content of 72 ppm fipronil were used in the tests described in the following Examples.

Stability

Long-term stability of a mixture prepared in this manner was determined by comparing analyses of a blend of three samples conducted immediately after preparation and three years after preparation. The initial content of fipronil was found to be 0.0073%, whereas the content after three years was found to be 0.0066%.

In contrast, a mixture 0.42% fipronil (as Regent 300 EC, from BASF) and 99.58% of 46-0-0 fertilizer initially contained 1048 ppm fipronil but after only one week at room temperature contained 930 ppm fipronil and after one week at 54° C. contained only 660 ppm fipronil.

Example 1

Plots of ca. 5000 ft$^2$ (ca. 465 m$^2$) and containing an average of nine fire ant mounds per plot were laid out and treated in late fall. Numbers of live mounds in each plot were counted prior to treatment. Three replicates of each treatment were tested. Granular formulations of fipronil and 15-2-15 fertilizer according to the invention were compared with granular formulations of fipronil on a Biodac® cellulose-based granular carrier. Efficacy was assessed at 30, 60, and 90 days after treatment ("DAT") (through mid-winter) by counting live mounds and calculating the percent reduction in mounds relative to the pretreatment counts. Results are presented in Table 1.

TABLE 1

In-field efficacy of granular fipronil formulations against red imported fire ant, *Solenopsis invicta*

|  |  |  |  | % reduction in fire ant mounds | | |
|---|---|---|---|---|---|---|
| Treatment | % active ingred. | Product applied | Active ingredient applied rate | 30 DAT | 60 DAT | 90 DAT |
| Control |  |  |  | 0% | 3% | 12% |
| Fipronil on Biodac | 143 ppm | 87 lbs/A (10 g/m$^2$) | 0.0125 lb/A (1.4 mg/m$^2$) | 13% | 24% | 38% |
| Fipronil on fertilizer | 72 ppm | 158 lbs/A (18 g/m$^2$) | 0.0125 lb/A (1.4 mg/m$^2$) | 30% | 42% | 41% |

The data in Table 1 show that fipronil on fertilizer formulation killed more ant mounds at 30 and 60 days after treatment than did the fipronil on Biodac granular carrier formulation.

Example 2

Plots size varied but each plot contained at least ten fire ant mounds per plot. The plots were treated in early summer. Numbers of live mounds in each plot were counted prior to treatment. Three replicates of each treatment were tested. Granular formulations of fipronil and 12-2-15 fertilizer according to the invention were compared with granular formulations of fipronil on a Biodac® cellulose-based granular carrier. Efficacy was assessed at 12, 29, and 104 DAT (through early fall) by counting live mounds and calculating the percent reduction in mounds relative to the pretreatment counts. Results are presented in Table 2.

TABLE 2

In-field efficacy of granular fipronil formulations against red imported fire ant, *Solenopsis invicta*

|  |  |  |  | % reduction in fire ant mounds | | |
|---|---|---|---|---|---|---|
| Treatment | % active ingred. | Product applied | Active ingredient applied rate | 12 DAT | 29 DAT | 104 DAT |
| Control |  |  |  | −6% | 24% | −12% |
| Fipronil on Biodac | 143 ppm | 87 lbs/A (10 g/m$^2$) | 0.0125 lb/A (1.4 mg/m$^2$) | 20% | 80% | 90% |
| Fipronil on fertilizer | 72 ppm | 158 lbs/A (18 g/m$^2$) | 0.0125 lb/A (1.4 mg/m$^2$) | 49% | 94% | 96% |

The data in Table 2 show that fipronil on fertilizer formulation killed more ant mounds at 12 and 29 days after treatment than did the fipronil on Biodac granular carrier formulation Example 3

Plots of ca. 5000 ft$^2$ (ca. 465 m$^2$) and containing an average of twenty-one fire ant mounds per plot were laid out and treated in late fall. Numbers of live mounds in each plot were counted prior to treatment. Four replicates of each treatment were tested. Granular formulations of fipronil and 0-0-7 fertilizer according to the invention were compared with granular formulations of fipronil on a Biodac® cellulose-based granular carrier. Efficacy was assessed at 1, 3, and 4 weeks after treatment ("WAT") by counting live mounds. Results are presented in Table 3.

TABLE 3

In-field efficacy of granular fipronil formulations against red imported fire ant, *Solenopsis invicta*

|  |  |  |  | fire ant mounds per plot | | | |
|---|---|---|---|---|---|---|---|
| Treatment | % active ingred. | Product applied | Active ingredient applied rate | 0 DAT | 1 WAT | 3 WAT | 4 WAT |
| Control |  |  |  | 22.0 | 34.8 | 27.3 | 35.8 |
| Fipronil on Biodac | 143 ppm | 87 lbs/A (10 g/m$^2$) | 0.0125 lb/A (1.4 mg/m$^2$) | 21.8 | 22.3 | 1.3 | 6.5 |
| Fipronil on fertilizer | 72 ppm | 158 lbs/A (18 g/m$^2$) | 0.0125 lb/A (1.4 mg/m$^2$) | 21.3 | 16 | 2.5 | 5 |

The data in Table 3 show that fipronil on fertilizer formulation killed more ant mounds at 1 week after treatment than did the fipronil on Biodac granular carrier formulation. At 3 weeks after treatment the efficacy of the two formulations was identical.

Example 4

Plots of ca. 5000 ft$^2$ (ca. 465 m$^2$) and containing an average of 44 fire ant mounds per plot were laid out and treated in spring. Numbers of live mounds in each plot were counted prior to treatment. Four replicates of each treatment were tested. Granular formulations of fipronil and 24-8-15 fertilizer according to the invention were compared with granular formulations of fipronil on a Biodac® cellulose-based granular carrier. Efficacy was assessed at 3, 7, and 14 days after treatment ("DAT") and at 1 and 2 months after treatment ("MAT") by counting live mounds. Results are presented in Table 4.

TABLE 4

In-field efficacy of granular fipronil formulations against red imported fire ant, Solenopsis invicta

| Treatment | % active ingred. | Product applied | Active ingredient applied rate | fire ant mounds per plot | | | | | |
|---|---|---|---|---|---|---|---|---|---|
| | | | | 0 DAT | 3 DAT | 7 DAT | 14 DAT | 1 MAT | 2 MAT |
| Control | | | | 43 | 43 | 47 | 58 | 74 | 46 |
| Fipronil on Biodac | 143 ppm | 87 lbs/A (10 g/m$^2$) | 0.0125 lb/A (1.4 mg/m$^2$) | 47 | 42 | 38 | 12 | 8 | 1 |
| Fipronil on fertilizer | 72 ppm | 158 lbs/A (18 g/m$^2$) | 0.0125 lb/A (1.4 mg/m$^2$) | 40 | 36 | 25 | 0 | 0 | 0 |

The data in Table 4 show that fipronil on fertilizer formulation killed more ant mounds at 3 and 7 days after treatment than did the fipronil on Biodac granular carrier formulation. By 14 days after treatment, fipronil on fertilizer had eradicated the fire ant mounds in the treated plots. An equivalent level of control was not observed in the fipronil on Biodac plots until two months after treatment.

What is claimed is:

1. An insecticidal fertilizer mixture comprising
   (a) an arylpyrazole of formula (I)

$$\text{(I)}$$

in which
X represents C—$R^6$,
$R^1$ is CN,
$R^2$ is $S(O)_n R^7$,
$R_3$ represents $NR^8 R^9$,
$R^4$ and $R^6$, independently of one another, represent hydrogen or halogen,
$R^5$ represents haloalkyl,
$R^7$ is alkyl or haloalkyl,
$R^8$ and $R^9$ independently represent hydrogen or alkyl, and
n represents 1;
   (b) a fertilizer;
   (c) a liquid adherent in which component (a) is dissolved, wherein the liquid adherent is a citric acid ester; and
   (d) optionally, one or more auxiliaries and/or carrier materials.

2. The mixture according to claim 1 in which
X is C—$R^6$,
$R^1$ is CN,
$R^2$ is $S(O)_n R^7$,
$R_3$ is $NH_2$,
$R^4$ and $R^6$, independently of one another, represent halogen,
$R^5$ is haloalkyl, and
$R^7$ is haloalkyl.

3. The mixture according to claim 1 wherein component (a) is 5-amino-1-(2,6,-dichloro-4-trifluoromethylphenyl)-4-trifluoromethylsulfinyl-3-cyanopyrazole.

4. An insecticidal fertilizer mixture according to claim 1 wherein the insecticidal fertilizer mixture is in the form of a stick, plate, tablet, or granule.

* * * * *